United States Patent [19]

Washington, deceased et al.

[11] Patent Number: 5,147,371

[45] Date of Patent: Sep. 15, 1992

[54] APPARATUS FOR REMOVING GALLSTONES AND TISSUE DURING SURGERY

[76] Inventors: Charles N. Washington, deceased, late of Lake Charles; by Virginia Y. Washington, executrix, 980 Terry La., Lake Charles, both of La. 70605

[21] Appl. No.: 723,057

[22] Filed: Jun. 28, 1991

[51] Int. Cl.⁵ .............................................. A61B 17/00
[52] U.S. Cl. .................................. 606/127; 606/114; 606/110; 606/113
[58] Field of Search ............... 606/110, 111, 112, 113, 606/114, 127, 128

[56] References Cited

U.S. PATENT DOCUMENTS

| | | | |
|---|---|---|---|
| 30,471 | 10/1860 | Dudley | 606/127 |
| 974,879 | 11/1910 | Gwinn | 606/113 |
| 1,609,014 | 11/1926 | Dowd | 606/114 |
| 4,997,435 | 3/1991 | Demeter | 606/127 |
| 5,074,867 | 12/1991 | Wilk | 606/127 |

FOREIGN PATENT DOCUMENTS 25796  1/1884  Brazil ................................ 606/127

OTHER PUBLICATIONS

Zucker, K. A. and Bailey, R. W., Atlas of Endo Cholecystectomy, 1990, pp. 1-14.

Primary Examiner—Stephen C. Pellegrino
Assistant Examiner—Glenn K. Dawson
Attorney, Agent, or Firm—Pravel, Gambrell, Hewitt, Kimball & Krieger

[57] ABSTRACT

A device for the in situ collection of surgically excised material, including whole gall bladder, gallstones, dissected gall bladder and other tissues, for removal from the body, particularly in laproscopic surgical procedures.

2 Claims, 1 Drawing Sheet

FIG.1
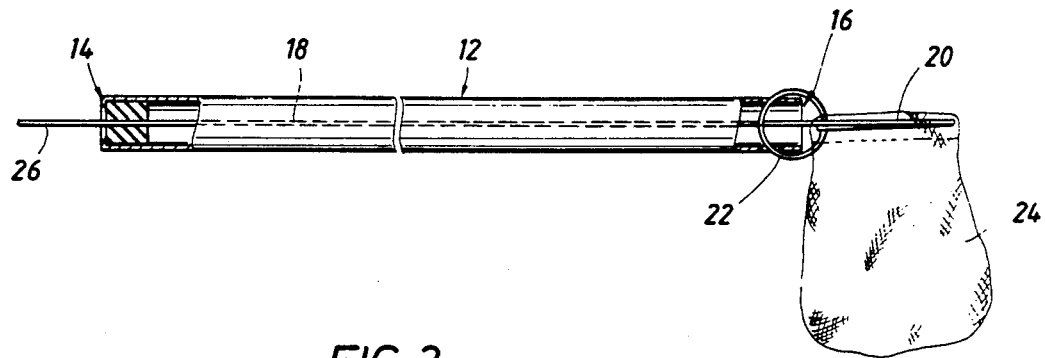
FIG.2
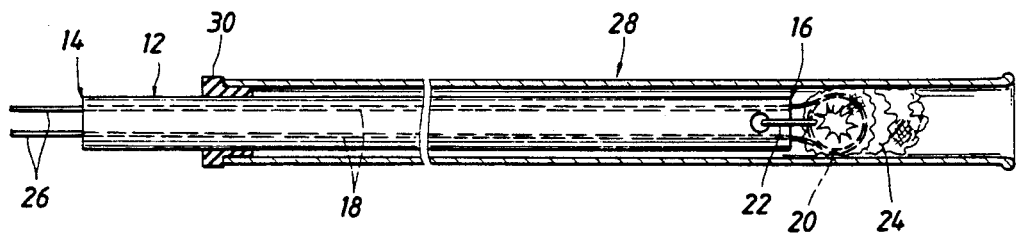
FIG.3
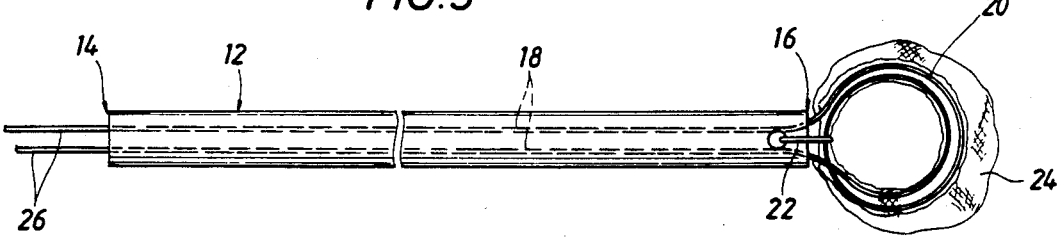
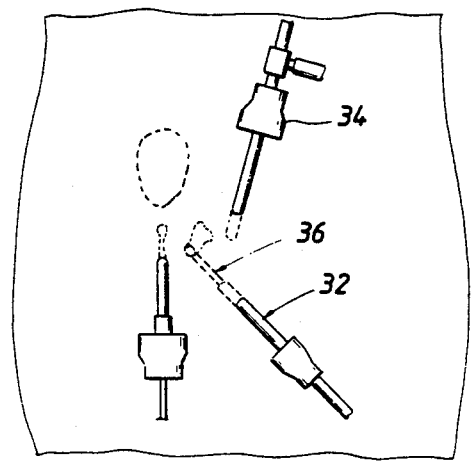
FIG.4

APPARATUS FOR REMOVING GALLSTONES AND TISSUE DURING SURGERY

FIELD OF THE INVENTION

The invention relates to a medical device for the removal of gallstones and/or gallbladder tissue, more particularly to a device particularly for use through an aperture or an opening in the patients abdomen or the like.

BACKGROUND OF THE INVENTION

Gallbladder disease continues to be one of the most common digestive disorders seen by physicians in this country. Approximately 500,000 cholecystectomies are performed each year in the United States. After conventional major abdominal surgery, patients experience considerable discomfort and their recovery time is lengthy. To address this problem, principles of laparoscopy have recently been applied to cholecystectomy.

Therapeutic laparoscopy for gallstone disease was reported by Morris in 1988 in which he described the procedure which allowed the laparoscopist to cannulate the gallbladder directly and remove gallstones, leaving the organ in situ. Laparoscopic removal of the gallbladder was initially performed in the U.S. by Saye and McKernan in 1988. Endocholecystectomy has evolved rapidly since 1988, along with the development of laparoscopic instrumentation and advances in video technology, contributing to the improved safety and quick adoption by general surgeons of this new procedure. Because of the tremendous advantages of endocholecystectomy, this procedure may rapidly replace open cholecystectomy as the procedure of choice.

In contrast to other, non-operative alternatives to the treatment of cholelithiasis, there are relatively few absolute contraindications to endocholecystectomy. This is because the surgeon can elect to convert the laparoscopic procedure to open cholecystectomy after an initial laparoscopic evaluation of the gallbladder and surrounding structures. Situations discovered at laparoscopy that may prompt such a decision include extensive adhesions caused by prior surgery or recurring attacks of cholecystitis, unusual vascular or ductal anatomy, other unsuspected pathology in the abdomen, acute inflammation, excessive bleeding, or the inability to safely identify the ductal or vascular anatomy.

Endocholecystectomy is performed under sterile conditions in a fully equipped operating room. In general, an operating laparoscope (generally 10 or 11 mm in diameter) with an attached camera is inserted through a canula to confirm intraperitoneal placement. Various laparoscopic instruments are then inserted through accessory canulae, to manipulate and dissect the gallbladder or other important anatomical structures.

Surgical procedures may be performed to excise and remove gallstones, rather than removing the entire gallbladder. To effect such removal, the gallbladder is opened, allowing stones to pass out of the gallbladder. The stones must then be removed from the abdomen. It is often difficult to collect stones, particularly when multiple stones are released, and successfully remove them from the abdomen.

The removal procedure generally requires removal of one stone at a time, relying on gentle vacuum to retain a stone at the tip of a vacuum tube for movement away from the gallbladder into an attached trocar for removal from the body. During this laborious task, stones are often lost within the body.

Procedures to remove the entire gallbladder are often hampered because the gallbladder is distended with bile or multiple stones and is too large to easily pass through a 10 mm or 11 mm surgical canula. In this situation, the surgeon may open the gallbladder to remove stones and aspirate fluid, collapsing or further dissecting gallbladder tissue prior to removal. Frequently during such manipulations stones are lost because of the difficulty in aspirating multiple stones being released from the gallbladder or multiple pieces of gallbladder tissue.

It would be of great utility to provide a device for retrieving and removing gallstones and gallbladder tissue during gallbladder surgery, particularly during laparoscopic endocholecystectomy.

SUMMARY OF THE INVENTION

A device according to the present invention collects gallstones and gallbladder tissue, retains stones and tissue until all have been excised and collected, and removes the collected stones and tissue from the body during surgery without loss of stones or tissues.

In the exemplary embodiment of the invention, the gallstone removal device is an elongated tube for insertion through a trocar sheath into the abdomen of a patient during gallbladder surgery. A single wire doubly traverses the tube, forming a full loop, preferably a double loop, at the end of the tubing *inserted into the abdomen. A bag or pouch extends from the wire loop which is tethered to the tube, and the loop and attached pouch are caused to open and close by manipulation of the wire.

In using a device according to the invention, the gallstone retrieval device is inserted via a trochanter into the abdomen. Once inside the body, the tube having the attached loop and pouch is pushed through the trochanter and into the body cavity. Pushing on the ends of the wires left outside the body causes the loop and its attached pouch to open. Gallstones, gallbladder tissue or other tissue samples are then collected in the open pouch. When removal is desired, the wires are pulled away from the tube, causing the loop and its attached pouch to close. The tubing and attached closed pouch containing gallstones or tissue are then pulled out of the abdomen without loss of stones or tissue during removal.

Other objects, features and advantages of the invention will be apparent from the following detailed description taken in connection with the accompanying drawings.

DESCRIPTION OF THE DRAWINGS

FIG. 1 is a side plan view in partial cross-section of the gallstone retrieval device.

FIG. 2 is a side plan view in cross-section of the gallstone retrieval device shown packaged within an insertion tube.

FIG. 3 is a top plan view of the gallstone retrieval device.

FIG. 4 is a perspective view of the gallstone retrieval device shown as it would be used during gallbladder surgery.

DETAILED DESCRIPTION OF THE INVENTION

Referring to FIGS. 1–4, the gallstone removal device includes an elongated tube 12 having a first end 14 and a second end 16. A wire 18 enters the tube 12 at the first end 14 and traverses the length of the tube to exit at the second end 16. The wire 18 is formed into a loop, preferably a double loop 20 having at least one full circle of wire after exiting the tube 12 at the second end, and reenters the tube 12 at the second end 16, traverses the length of the tube 12, and exits the tube 12 at the first end 14, the initial site of entry. The loop 20 is tethered to the tube 12 at the second end 16, for example, by a fastener 22, e.g. a loop of string, wire or the like. The fastener 22 prevents the loop 20 from entering the tube 12 and also permits expansion or enlargement and contraction or reduction of the loop 20 in response to pushing or pulling on the free ends 26 of the wire 18 at the opposite end 14 of the tube 12. The fastener 22 firmly attaches the loop 20 to the tube, however movement of the wire 18 is not impeded. A fabric extends from the loop 20 creating a bag or pouch 24, with the loop 20 acting as a drawstring for the pouch 24 such that enlarging the loop 20 opens the pouch 24, and closing the loop 20 closes the attached pouch 24.

The arrangement of the wire 18, loop 20, fastener 22, and pouch 24 is such that pushing on the ends 26 of the wire 18 in the direction of the tube 12 causes the loop 20 and the attached pouch 24 to open and pulling on the ends 26 of the wire 18 in the direction away from the tube 12 causes the loop 20 and the attached pouch 24 to close.

As shown best in FIG. 2, the gallstone retrieval device is packaged prior to use within an insertion tube 28 for insertion into the abdomen. The loop 20 is in a closed position and the pouch 24 is folded to compact the device within the insertion tube 28. The device is sealed from the exterior within the insertion tube 28, for example by a rubber stopper 30. The insertion tube 28 is shorter in length and slightly larger in diameter than the elongated tube 12 of the device, but is of a size sufficient to accomodate the device and to be inserted through a laproscopic trochanter for insertion into the abdomen. The packaged insertion tube 28 may then be directly inserted through an incision in the abdomen, or preferably, is inserted through a surgical trochanter 32.

Referring to FIG. 4, the general method of using a device according to the invention is now described. A laparoscope 34 is inserted through an incision into the abdomen. Similarly, surgical instruments such as a surgical clipper may be inserted through accessory openings in the abdomen. The device of the invention, the gallstone retrieval device 36 packaged within its insertion tube 30, may likewise be inserted through an accessory opening in the abdomen, generally through a typical laproscopic trocar 32. Once inserted, the device is pushed through the open end of the insertion tube, releasing the loop 20 and attached pouch 24 into the body cavity. Within the body cavity, the pouch is opened, for example, by pushing on the ends 26 of the wire 18 which traverses the tube 12.

Gallstones removed from the gallbladder, the gallbladder itself, or pieces of tissue for removal from the abdomen are collected in the open pouch 24. In general, a surgical tool such as a gentle aspirator may be used to remove the stones or tissue from their in situ position and place them inside the pouch 24 of the device. When all tissue and stones have been collected, the pouch 24 is closed to prevent loss of stones and tissue, for example, by pulling on the ends 26 of the wire 18 which traverses the tube.

The closed pouch 24, containing the collected stones and tissue is then withdrawn through the opening in the abdomen. If required, the incision may be enlarged to facilitate removal of the filled pouch.

Using the device of the present invention, it is not required that an aspirator be used to remove tissue or stones through a trochanter. This greatly reduces the likelihood of complications due to dislodging and dropping stones or tissue, as discussed above. Stones or tissue are simply transferred in the insufflated abdomen to the pouch 24, a short distance, and a path having many fewer chances for dislodging the stone or tissue.

The device may be fabricated of many types of materials, providing that the components are sterilizable. Highly biocompatible materials are not required because the device is inserted for only a relatively short period. The tube 12, for example, may be fabricated of copper, and may be approximately 4 mm in diameter. Preferably, the device is of a size that can be inserted into a surgical trochanter such as those generally available for laparoscopic procedures. The pouch 24 bag may be fabricated of netting materials, for example, nylon, marlex, prolene, and the like, with the proviso that the material have a marginal amount of memory sufficient to form the needed pouch or bag shape within the abdomen without requiring arrangement by the surgeon. A useful, readily available material is commonly known as bridal netting. The wire 18 may be plain or coated, straight or braided, with the proviso that wire be both sufficiently rigid to permit push and pull movements and sufficiently flexible permit opening and closing of the loop 20. In the preferred embodiment, the wire is coated with plastic. One such commonly available wire is 60 pound, plastic-coated fishing leader.

The fastener 22 may be of common surgical string or may be of a more durable material such as wire. If surgical string is utilized, it may be preferable to have the surgeon install the fastener 22 while the device is located in the abdomen, simplifying packaging of the device in the insertion tube 28.

Having described the invention above, various modifications of the techniques, procedures, material and equipment will be apparent to those in the art. It is intended that all such variations within the scope and spirit of the appended claims be embraced thereby.

I claim:

1. An apparatus for the in situ collection of surgically excised material comprising:
    an elongated tube having a first end and a second end;
    a wire entering said tube at said first end, traversing the length of said tube, exiting said tube at said second end, forming a loop at said second end, reentering the tube at said second end, and again traversing said tube, wherein said loop includes at least a full circle of said wire;
    means for fastening said full circle of said loop to said elongated tube at said second end to retain said loop substantially at said second end and yet allow enlargement of said loop; and
    a collection pouch having an openable mouth and means at said openable mouth for encircling said loop, wherein said loop acts as a drawstring for said pouch and the size of said loop generally defines the opening size of said openable mouth of said pouch.

2. An apparatus for the in situ collection of surgically excised material comprising: an elongated tube having a first end and a second end; a wire entering said tube at said first end, traversing the length of said tube, exiting said tube at said second end, forming a loop at said second end which includes at least a full circle of said wire, reentering the tube at said second end and again traversing the length of the tube to exit at the site of entry; and a collection pouch having an openable mouth and means at said openable mouth for encircling said loop, wherein said loop acts as a drawstring for said pouch and the size of said loop generally defines the opening size of said openable mouth of said pouch.

* * * * *